US00PP20500P2

(12) United States Plant Patent
Riker

(10) Patent No.: US PP20,500 P2
(45) Date of Patent: Nov. 24, 2009

(54) CHERRY TREE NAMED 'RR2A'

(50) Latin Name: *Prunus avium L.*
Varietal Denomination: RR2a

(76) Inventor: Russell Riker, 4112 Jagla Rd., Wenatchee, WA (US) 98801

( * ) Notice: Subject to any disclaimer, the term of this patent is extended or adjusted under 35 U.S.C. 154(b) by 0 days.

(21) Appl. No.: 12/217,500

(22) Filed: Jul. 2, 2008

(51) Int. Cl.
*A01H 5/00* (2006.01)

(52) U.S. Cl. ..... Plt./181

(58) Field of Classification Search ..... Plt./181
See application file for complete search history.

(56) References Cited

U.S. PATENT DOCUMENTS

PP15,386 P2 11/2004 Brown

*Primary Examiner*—Annette H Para
(74) *Attorney, Agent, or Firm*—Christensen O'Connor Johnson Kindness PLLC

(57) ABSTRACT

A new and distinct variety of cherry tree, *Prunus avium L.*, denominated RR2a, which is similar to Bing (not patented) and Staccato (not patented) but which matures in mid August and has very firm fruit with high titratable acids, and a long storage life in common cold storage.

5 Drawing Sheets

Latin name of the genus and species claimed: *Prunus avium L.*

Variety denomination: 'RR2a'.

BACKGROUND OF THE INVENTION

The distinct and new variety of cherry tree was discovered by Russell Riker in about 1998 in a block of "Bing" cherries (unpatented) that had been planted in 1971 at an orchard in Wenatchee Heights Orchard, Chelan County, Wash. Cherries of this "mother" tree were noted to mature nearly a month later than cherries of the adjacent Bing trees. The mother tree was named "RR2a." The new variety was asexually reproduced by grafting at the orchard in Wenatchee, Wash. More specifically, in 1999 two second generation trees were grafted on mazzard root stock, and in 2000 seven third generation trees were grafted on mazzard root stock. Fruit from the second and third generation trees has been observed from 2004 to present and been found to be consistent with the fruit of the mother tree. The mother tree was at first thought to be a whole tree mutation. However, S-allele testing conducted in 2008 determined that the RR2a trees have the S-allele genotype $S_3S_4'$ such that it was not possible that the RR2a originated as a bud spore of Bing. The tree therefore is believed to be a chance seedling. No commercial propagation nor distribution has been carried out.

BRIEF SUMMARY OF THE INVENTION

The new variety is similar to Bing cherry with respect to tree morphology dealing with wood, leaves, bloom and tree growth habit. Fruit shape is also similar to Bing cherry fruit, as is the pH of mature fruit, but the RR2a differs from Bing in maturity date (approximately 36 days later), firmness (approximately twice as firm), and sugar content (approximately 1.4. lower sugar content). The new variety also has been compared to "Staccato" (unpatented) grown near the same location and been found to have lower fruit pH readings than Staccato cherry, similar levels of fruit sugar content, but much firmer than Staccato. RR2a also matures approximately 10 days following Staccato. RR2a is unique in that it will maintain its firmness for up two months in cold storage.

BRIEF DESCRIPTION OF THE DRAWINGS

The accompanying photographs show the following characteristics of this new variety:

FIG. 5 is a chart comparing characteristics of RR2a, Bing, and Staccato cherries (firmness ratings were measured using a Firm Tech firmness tester and ratings are in milligrams needed to depress 1 mm).

DETAILED BOTANICAL DESCRIPTION

Figure 1:
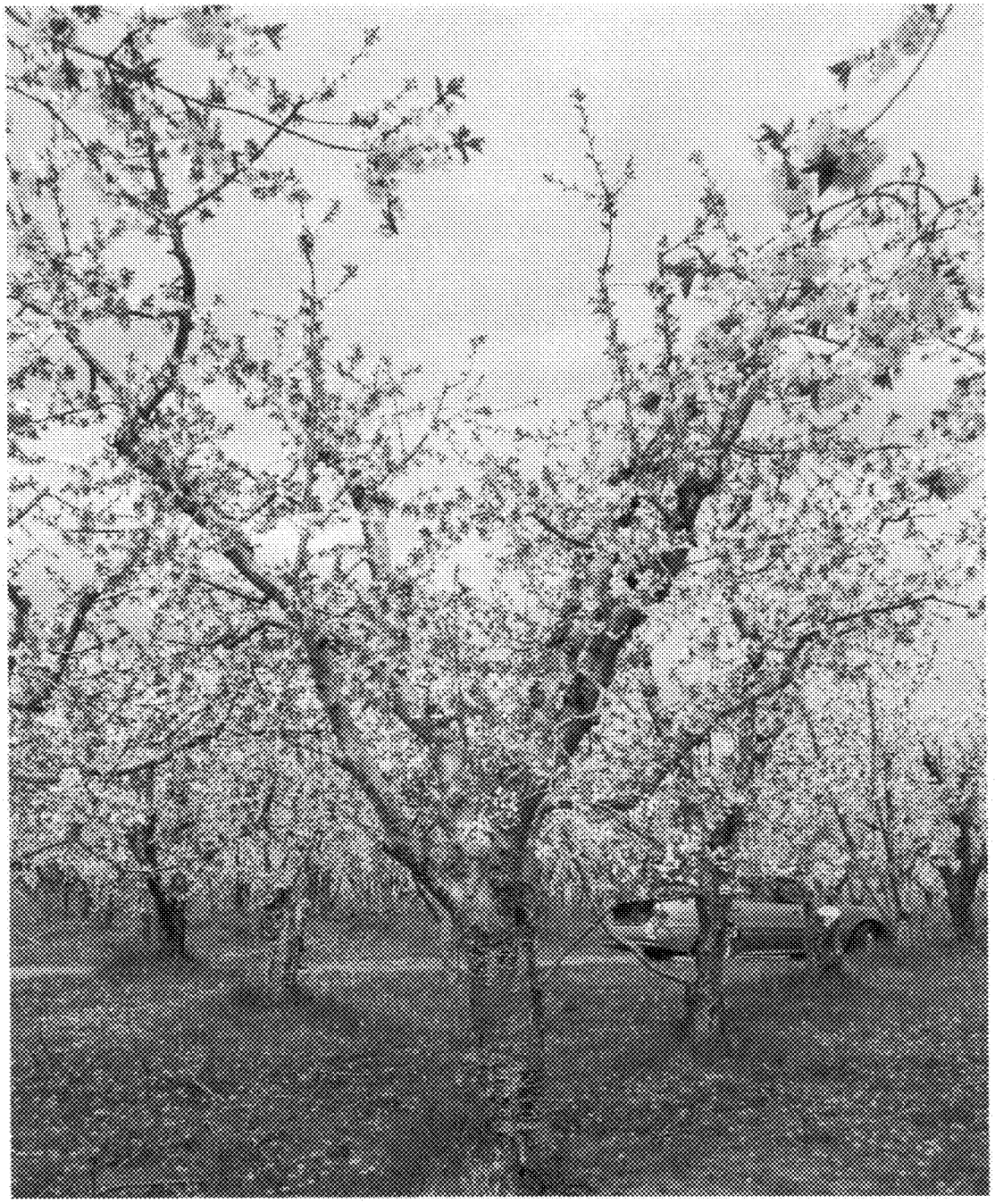
FIG. 1 is a photograph of the RR2a mother tree during bloom.
Figure 2:
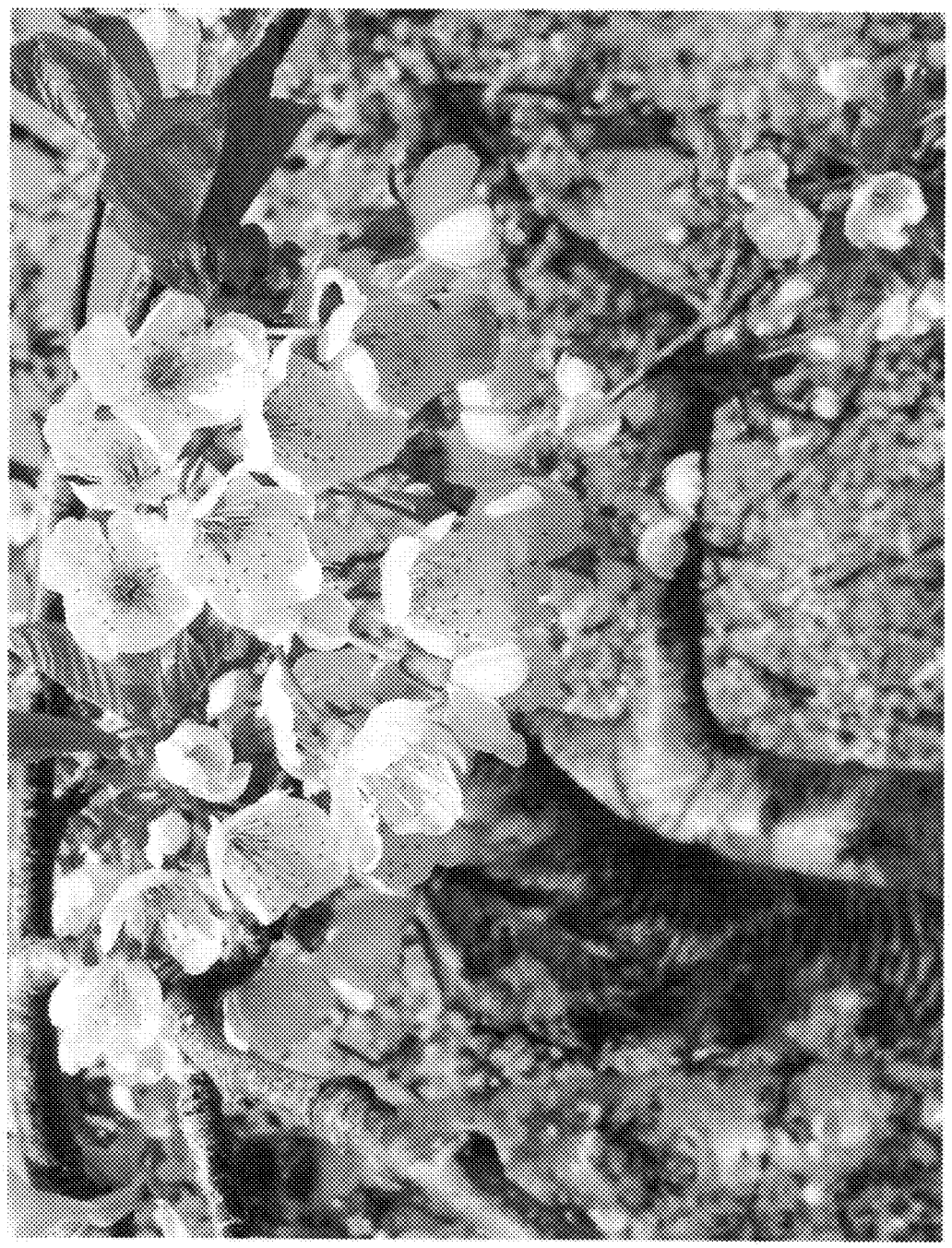
FIG. 2 is a photograph of a blooming cluster from the RR2a mother tree.
Figure 3:
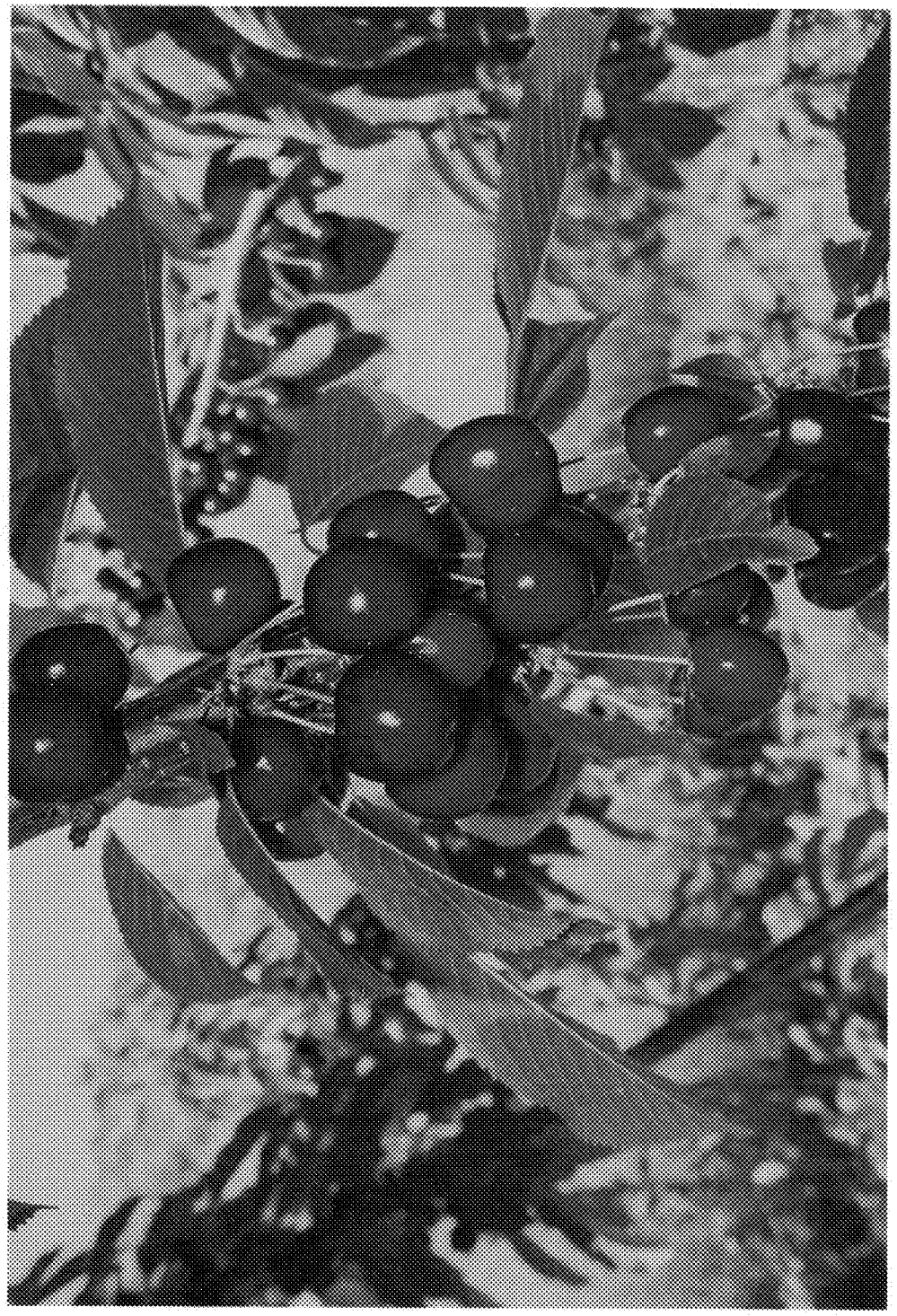
FIG. 3 is a photograph of a fruiting limb of the RR2a mother tree at harvest maturity.
Figure 4:
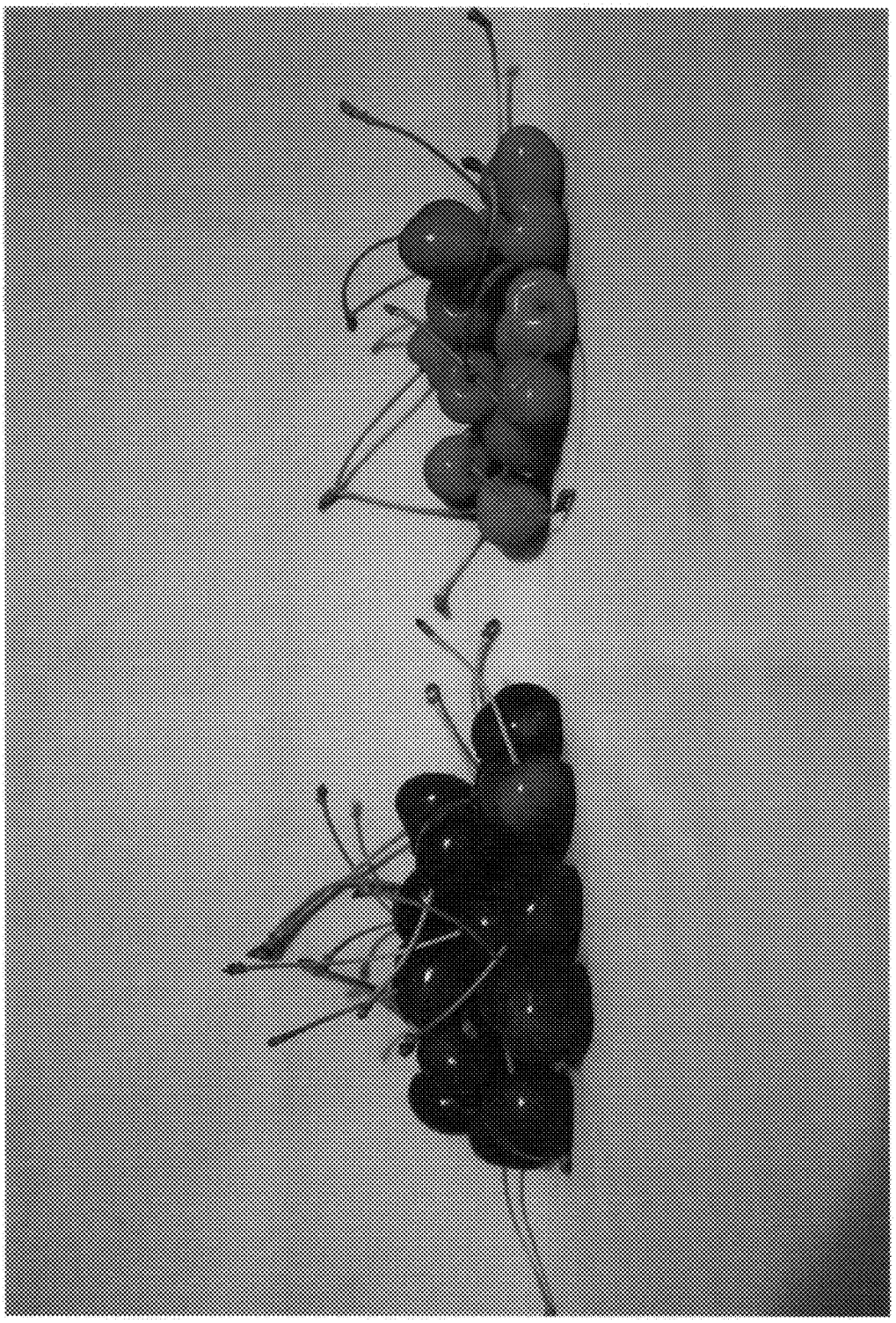
FIG. 4 is a comparison photograph of Bing cherries and RR2a cherries.

The following detailed description of the characteristics of the new variety of cherry tree is based on observations of the second and third generation trees during the 2004–2007 seasons at Wenatchee Wash., unless indicated otherwise. Color terminology is in accordance with The Royal Horticulture Society Colour chart (see www.rhs.org.uk/Learing/Publication/pubs_library_colorchart.htm).

Tree:

*Size.*—Medium large for cherry (21 ft. tall by 18 ft. wide when trained to open upright steep leader); the same as the adjacent Bing cherry trees; moderately vigorous (average growth of mother tree is 30 cm); branching habit is upright and spreading out at 45°.

*Density.*—Moderate; forms many spurs.

*Form.*—Upright and moderately spreading habit.

*Hardiness.*—Hardy in area where discovered and tested; same as for Bing and Staccato cherry trees.

*Production.*—Considered moderate to moderately heavy; same as for Bing cherry.

*Bearing.*—Regular and consistent.

*Trunk size.*—Moderately stocky (26.7 cm in diameter at 46 cm above soil line).

*Trunk bark texture.*—Medium with smooth areas; typical for sweet cherry.

*Trunk bark color.*—From the greyed-purple group N186C.

*Trunk lenticels.*—Numerous, rough, large (averaging 2.6 cm long and 0.64 cm wide), color is from the white group N155a.

Branches:

*Branch size.*—Scaffold branches are stocky, averaging 15.6 cm in diameter; fruiting branches are thin, averaging 0.52 cm in diameter; current (first year) branches are thin, averaging 0.47 cm in diameter.

*Branch texture.*—Smooth, typical for sweet cherry.

*Branch color.*—Color of scaffold branches is from the grade-red group 178A; color of the fruiting branches is from the brown group 200B; color of the current branches is from the greyed-brown group 199A.

*Branch lenticels.*—Lenticels are numerous on scaffold branches averaging 1.64 cm long by 0.51 cm wide with color from the greyed-white group 156C; for fruiting branches, lenticels are present averaging approximately 8 per linear cm and of a size approximately 1 mm wide by 1.7 mm long with color from the white group N155A; lenticels are present on first year branches but small (averaging 1 mm in diameter and approximately 8 per linear cm) with color from the white group N155A.

Leaves: Measurements are from the mid-point of actively growing 2007 season's growth at harvest maturity:

*Size.*—Medium large, averaging 12.2 cm long by 7.0 cm wide.

*Form.*—Oval in shape with a mucronate tip and rounded base.

*Color.*—From the yellow-green group, upper surface is 147A, lower surface is 174B.

*Mid-vein.*—Large, 2 to 3 mm in diameter, underside color from the yellow-green group 145A.

*Petiole.*—Medium in length averaging 3.6 cm, upper surface from the greyed-purple group 187B, lower surface from the yellow-green group 146C.

*Leaf texture.*—Smooth.

*Margin.*—Crenate to finely serrate.

*Glands.*—Variable in number (2 to 5) averaging 2.7 per petiole, oval in shape 1.5–2.5 mm wide by 3 mm long, positioned both opposite and alternate on rim of petiole groove starting 5 to 10 mm from blade.

*Stipules.*—Present average 15 mm in length.

Flower buds:

*Measurements are from the* 2007 *growing season.*—Hardy, plump and conical, medium size (5.02 mm to 8.12 mm).

Flowers:

*Measurements are from the* 2007 *growing season.*—Self-fertile, consistent with S-allele genotype $S_3S_4$'.

*First bloom.*—Apr. 22, 2007 (full bloom on Apr. 27, 2007).

*Size.*—Large, averaging 3.8 cm in diameter.

*Color.*—White.

*Bloom count.*—Average 3.4 per bud.

*Petals.*—Average length 15.9 mm, average width 13.4 mm, color is white.

*Nectaries.*—Color is in the yellow-green group 144B.

*Anthers.*—Small, oval in shape, 0.5 mm by 1.0 mm, color is in the greyed-orange group N167B.

*Pollen.*—When mature, color in the yellow-orange group 14B.

*Pedicel.*—Average length 36.4 mm; color in the yellow-green group 144D.

*Sepals.*—Curled backwards and flat against the pedicel, color is in the yellow-green group 143D, with moderate surface and tip highlights in the red-purple group 59B.

Fruit:

*Maturity.*—Harvest date August 17 (5 year average 2001–2005).

*Size.*—Large, diameter transversely across suture average 2.7 cm; diameter apically averaged 2.6 cm.

*Form.*—Uniform, more reniform than round.

*Suture.*—Very shallow, not raised; is slightly darker than the skin.

*Base.*—Rounded.

*Apex.*—Rounded pistil point, slightly indented.

*Stem.*—Moderate in length (average length 4.3 cm), thin, color from the green group 138C.

*Skin.*—Medium thickness, medium texture, tenacious to flesh, color from the greyed-purple group 187B.

*Flesh color.*—From the red-purple group 59B.

*Flesh texture.*—Firm and crisp.

*Fibers.*—Moderate in number.

*Ripens.*—Moderately evenly.

*Flavor.*—Sweet and low acid.

*Aroma.*—Slight.

*Eating quality.*—Good.

*Pit cavity.*—Color from the purple group N77A.

Stone:

*Type.*—Very shallow, semi-free.

*Size.*—Medium, average 11.5 mm long by 10.9 mm wide.

*Form.*—Oval, rounded base, oblong helium, round to round-conical apex.

*Sides.*—Equal.

*Surface.*—Smooth.

*Ventral edge.*—1 mm wide narrow suture that is subtended by two low ridges converging basally and apically that averages 6 mm wide at the midpoint.

*Dorsal edge.*—Sharp, smooth, slightly raised ridge from base to apex.

*Color.*—From the greyed-orange group 164C.

*Tendency to split.*—None.

Use: Late season premium fresh market;

Keeping quality: Very good, up to 30 days in common refrigerated storage;

Resistance to insects and diseases: Shows no unusual susceptibility nor resistance to any disease and/or plant or fruit pests of sweet cherry found in central Washington State;

Shipping quality: Excellent;

Variance in botanical details: RR2a exhibits the above-described characteristics as grown in Wenatchee, Chelan County, Wash. It is expected that differences may occur when grown in areas exhibiting different growing conditions.

I claim:

1. A new and distinct variety of cherry tree as herein shown and described.

* * * * *

| Variety | Harvest Date | Size Range | Peak Size | Average Brix | pH | Firmness Range | Average Firmness |
|---|---|---|---|---|---|---|---|
| Bing | 7/10/2007 | 9 - 10.5 | 9.5 | 20.2 | 3.72 | 163 - 329.1 | 246 |
| RR2a | 8/16/2007 | 9 - 10 | 9.5 | 18.8 | 3.74 | 375 - 686.3 | 485.1 |
| Staccato | 8/6/2007 | 8.5 - 10 | 9 | 18.4 | 3.87 | 293.3 - 456.6 | 373 |
| | | | | | | | |
| RR2a (after cold Storage) | 10/18/2007 (from cold Storage) | 9 - 10 | 9.5 | 18.6 | 4.45 | 367.5 - 692.7 | 473.9 |

*Fig.5.*